United States Patent
Dauer et al.

[11] Patent Number: 6,134,471
[45] Date of Patent: Oct. 17, 2000

[54] RATE ADAPTIVE PACEMAKER

[75] Inventors: Wolfgang Dauer, Forchheim; Thomas Wetzig, Bubenreuth; Ronald Fröhlich, Erlangen, all of Germany

[73] Assignee: Biotronik Mess- und Therapiegeräte GmbH & Co. Ingenieurbüro Berlin, Berlin, Germany

[21] Appl. No.: 09/175,996

[22] Filed: Oct. 21, 1998

[30] Foreign Application Priority Data

Oct. 23, 1997 [DE] Germany ............................ 197 47 820

[51] Int. Cl.[7] .................................................. A61N 1/365
[52] U.S. Cl. ................................................................ 607/17
[58] Field of Search ........................................ 607/17, 26

[56] References Cited

U.S. PATENT DOCUMENTS

| | | |
|---|---|---|
| 4,712,555 | 12/1987 | Thonander et al. . |
| 4,766,900 | 8/1988 | Callaghan .................................. 607/26 |
| 4,870,974 | 10/1989 | Wang . |
| 4,919,137 | 4/1990 | Schaldach . |
| 4,936,304 | 6/1990 | Kresh et al. . |
| 4,972,834 | 11/1990 | Begemann . |
| 5,085,215 | 2/1992 | Nappholz . |

FOREIGN PATENT DOCUMENTS

| | | |
|---|---|---|
| 0232528A2 | 8/1987 | European Pat. Off. . |
| 0294949A1 | 12/1988 | European Pat. Off. . |
| 0310216A2 | 4/1989 | European Pat. Off. . |
| 0232528B1 | 9/1992 | European Pat. Off. . |
| 0545628A2 | 6/1993 | European Pat. Off. . |
| 0237767B1 | 9/1993 | European Pat. Off. . |
| 0716864A2 | 6/1996 | European Pat. Off. . |
| 0796636A1 | 9/1997 | European Pat. Off. . |
| 0798015A2 | 10/1997 | European Pat. Off. . |
| 3545359A1 | 6/1987 | Germany . |
| 92/05836 | 4/1992 | WIPO . |

OTHER PUBLICATIONS

"Frequenzadaptive Herzschrittmacher" by K Stangl et al. pp. 255–271.

*Primary Examiner*—Jeffrey R. Jastrzab
*Attorney, Agent, or Firm*—Venable; George H. Spencer; Robert Kinberg

[57] ABSTRACT

A rate-adaptive pacemaker, comprising a stimulation pulse generator and therewith connected output means for stimulating at least the heart ventricle of a heart-signal input stage in order to detect the signal shape of evoked heart signals, particularly the morphology of the ventricular evoked response VER, also comprising a rate-calculation unit that is connected on the input side with the heart signal input stage and on the output side with the stimulation pulse generator, for calculating the stimulation rate based on the physiological stress on the pacemaker carrier and for emitting a rate-control signal, wherein the rate calculation device generates the rate-control signal on the basis of the heart signal shape detected at the input stage. The rate-calculation unit has a signal amplitude processing unit for calculating the rate-control signal upon responding to heart signal amplitude values at predetermined times during a specified heart cycle, in particular the last preceding heart cycle.

18 Claims, 8 Drawing Sheets

RATE ADAPTIVE PACEMAKER

FIELD OF THE INVENTION

The invention relates to cardiac pacemakers and, in particular, to a rate-adaptive pacemaker.

BACKGROUND OF THE INVENTION

A multitude of different rate-adaptive pacemaker designs have been known and used clinically for years, for which the stimulation frequency or stimulation rate is adjusted in dependence on signals recorded inside the patient's body, which reflect the patient's physiological requirement with respect to the cardiac activity. An overview of the goals pursued in the development of rate-adaptation in pacemaker technology and the paths taken is provided in the relatively early standard work by K. Stangl et al.: Frequency Adaptive Pacemakers, Darmstadt, 1990.

The so-called QT pacemaker is also discussed in this work (pages 255–272), for which the stimulation rate is adjusted with the aid of the time interval between a stimulation pulse and the appearance of the T-spike of the ventricular cardiac action signal that is initiated (evoked) by the stimulus, the so-called QT interval. This interval can be used for the rate control of a pacemaker because it depends on the cardiac frequency as well as the stress and because the dependence on the cardiac frequency is nearly linear, at least for a specific time range. The disadvantages in this case include the detection and analysis of the T-component of the intracardiac ECG, which is rather problematic in practical operation owing to the low signal amplitude and not very distinctive signal shape and, above all, the danger of positive feedback based on the fact that an increase in the stress as well as the frequency leads to a shortening of the QT interval.

According to EP 0232 528 B1 and the EP 0237 767 B1, the stimulation rate is controlled by a comparison between an integrated cardiac action potential and a predetermined target value or comparison value. On closer examination, the procedure amounts to an analysis of the time interval, starting with the stimulus, to the end of the R-spike of the ventricular ECG ("depolarization gradient duration"). However, in practical operation this signal duration cannot be determined with any reliability for a signal encumbered with interference and, especially, with zero line fluctuations.

Thus, it is the object of the invention to provide a rate-adaptive pacemaker of the aforementioned generic type with improved usefulness in practical operations.

SUMMARY OF THE INVENTION

This object is solved with a pacemaker having a stimulation pulse generator for stimulating at least the ventricle of a heart; output means connected to said stimulation pulse generator for supplying a stimulation pulse to said heart; a heart-signal input stage for detecting the shape of evoked heart signals; a rate calculation device, receiving as input an output from said heart-signal input stage and providing an output to said stimulation pulse generator, said output including a rate-control signal, said rate calculation device calculating a stimulation rate based on physiological stress of an individual in whom the pacemaker is implanted and including a signal-amplitude processing unit for calculating the rate-control signal in response to heart signal amplitude values at predetermined times during a specified heart cycle, said heart signal amplitude values derived in connection with said shape of evoked heart signals.

In order to control the stimulation rate, the invention includes the technical teaching of using stress-dependent, characteristic changes in the signal morphology of an evoked heart signal, which changes are not critically distorted even by interference and zero line drifts.

Two so-called difference points (points in time starting with the stimulus) are determined for a rate adaptation. At these two difference points, a difference value is formed from the heart signal voltage values (specifically, from the so-called VER =ventricular evoked response) which for a physiological beat frequency has a known relationship to the beat frequency. This difference serves as a parameter for the frequency adaptation, and it increases above the frequency-dependent desired difference if the stimulation frequency is too low, or drops below the frequency-dependent desired difference if the stimulation frequency is too high. The difference points determined during an initial calibration remain constant and are not adjusted to rate changes.

The first difference point corresponds to the T-wave maximum (T+) at maximum stress and adapted stimulation frequency. The point selected as the second difference point is the one for the highest difference in the R+ wave range between the VER curve course with maximum stress for the adapted frequency and the VER curve course for the resting position, for the same frequency. It is necessary to measure these two curves for the calibration.

A further improvement in the rate adaptation algorithm can be achieved by including the actual signal duration. For this, the point in time for a characteristic signal point, e.g., the T+ amplitude, is determined (for example, through differentiation) for each signal used for the frequency adaptation in addition to the signal voltage at the two difference points. The distance between this point in time and the second difference point is determined to be the difference k. The improved rate-adaptation parameter is then calculated advantageously in such a way, for example, that the difference between the signal voltages at both difference points is divided by $k^2$.

BRIEF DESCRIPTION OF THE DRAWINGS

Further explanation of the invention will be given below, in the form of a description of preferred embodiments of the invention, taken in combination with the accompanying drawings, in which.

DETAILED DESCRIPTION OF THE INVENTION

Figure 1:
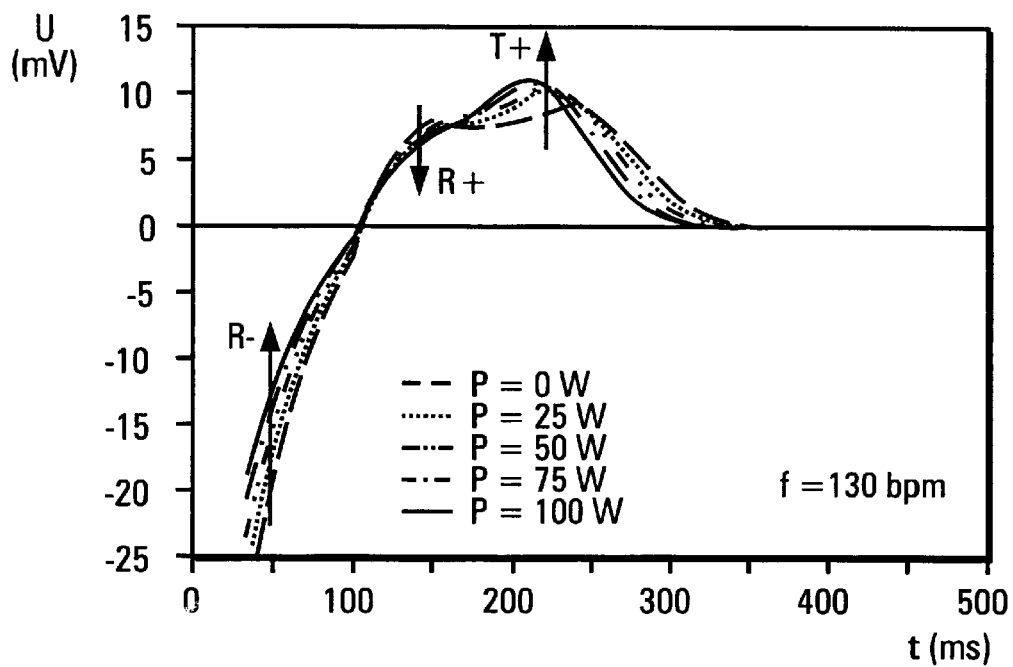
FIG. 1 is a representation of the dependence of the VER on stress.

FIG. 1 illustrates the stress-dependence of the VER signal morphology for a stress that increases from the rest position to 100 W and is obtained with the aid of a bicycle ergometer test. The stimulation frequency f was kept constant at 130 bpm; and the signal voltage U for the time interval t is plotted, starting with the stimulus pulse. The curves show that the signal voltage in the R− segment as well as in the T+ segment of the VER increases with increasing stress, whereas it decreases in the R+ range with increasing stress. It is obvious from this that an analysis of the signal morphology for the stimulation rate control appears advantageously possible, based on a comparison of the signal amplitude in the R− range or the T+ range with that in the R+ range.

Figure 2:
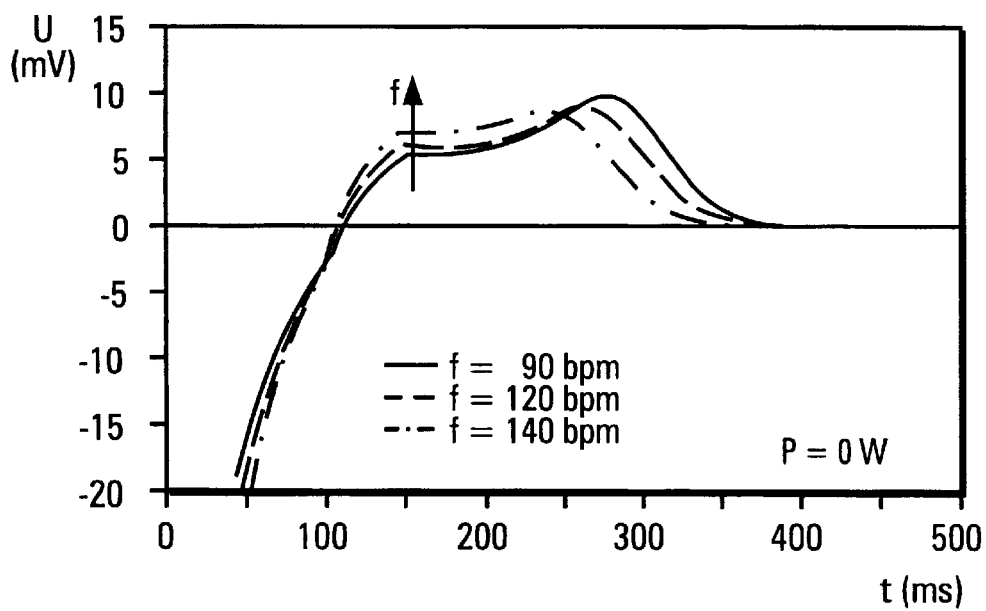
FIG. 2 is a representation of the dependence of the VER on the stimulation frequency.

FIG. 2 is a representation of the dependence of the VER on the stimulation frequency when the patient is resting, wherein the signal voltage U is again plotted for the time interval t, starting with the stimulus pulse, that is with the same scale division as in FIG. 1. It is clear from this that the VER morphology also depends on the frequency.

Figure 3:
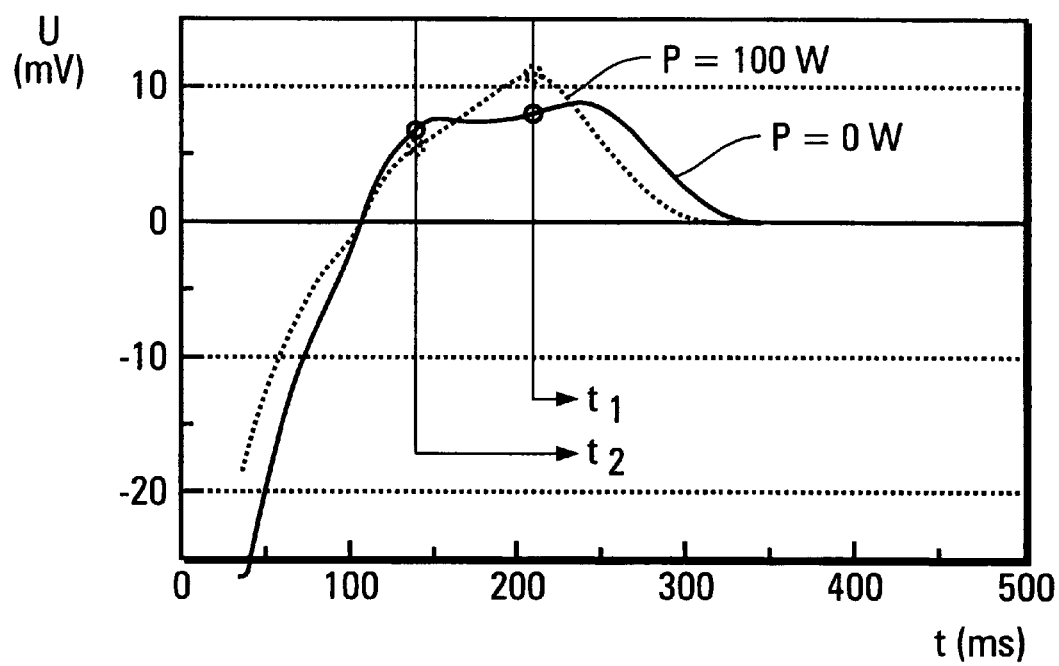
FIG. 3 is a representation of a signal morphology analysis of the VER for the rate control.

FIG. 3 is a representation of the signal morphology analysis of the VER for the rate control, where two points in time $t_1$ and $t_2$ are plotted for two VER signal curves, singled out as examples. The signal amplitudes for these points in time are determined and the times are selected in such a way that the amplitude difference, which serves as the parameter Par used for the rate adaptation, has the highest possible stress-dependent dynamic.

Figure 4:
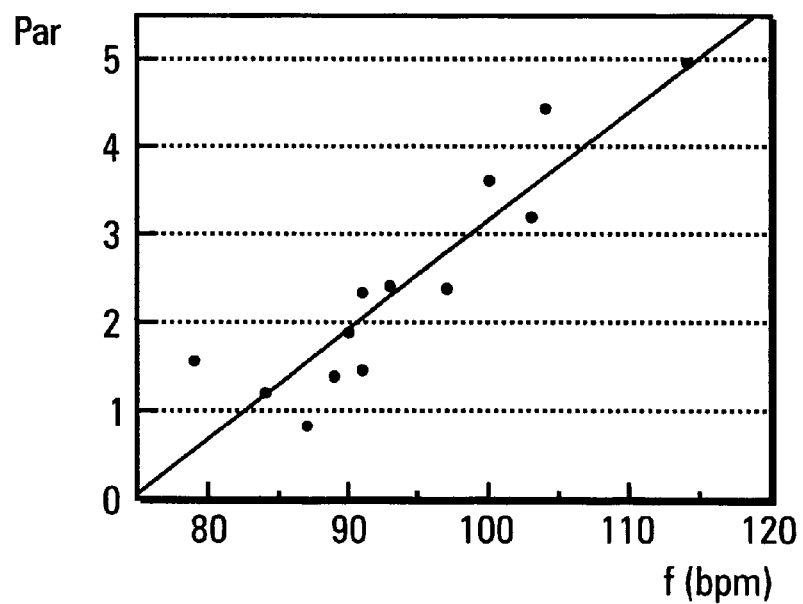
FIG. 4 is a representation of the correlation between adaptation parameters and stimulation frequency for one embodiment of the invention.

The graphic representation of the correlation between adaptation parameter Par (in optional units) and stimulation frequency f, shown in FIG. 4, clearly demonstrates the nearly linear dependence of the adaptation parameter. The straight line for the linear regression illustrates the physiological course. Thus, a linear physiological course can be indicated for the adaptation parameter. Parameter values above the physiological course point to a low stimulation, meaning a stimulation frequency that is too low for the present stress. Values below the physiological course point to an overstimulation. Thus, it is possible to determine the necessity for a change in the stimulation frequency by comparing the actual parameter value to the "desired value" that corresponds to the physiological course.

Figure 5:
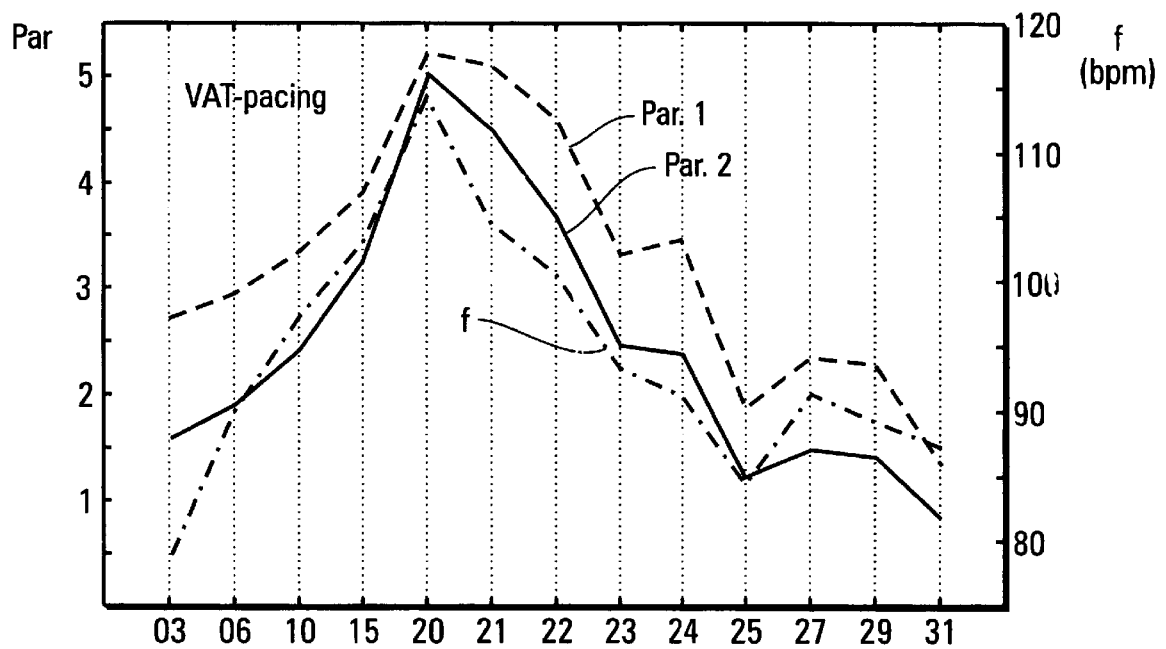
FIG. 5 is a comparative representation of the time-dependent course of the stimulation frequency, as well as a first and a second rate-adaptation parameter.

A comparative representation in FIG. 5 shows the time-dependent courses of the stimulation frequency (dash-dot curve), as well as a first rate-adaptation parameter, determined according to FIG. 4, and a second rate-adaptation parameter according to the illustration nearer the top, which is defined more precisely by including the VER signal width (dashed or continuous curve—optional units) for a specified stress-time-program. The comparative representation shows that a stress-dependent control of the stimulation rate is possible with good to excellent approximation by using a rate-adaptation parameter that is derived from the VER signal morphology. A correlation coefficient of 0.852 was determined for the correlation of the first adaptation parameter and the stimulation frequency, and a coefficient of 0.914 was determined for the improved, second parameter.

Figure 6:
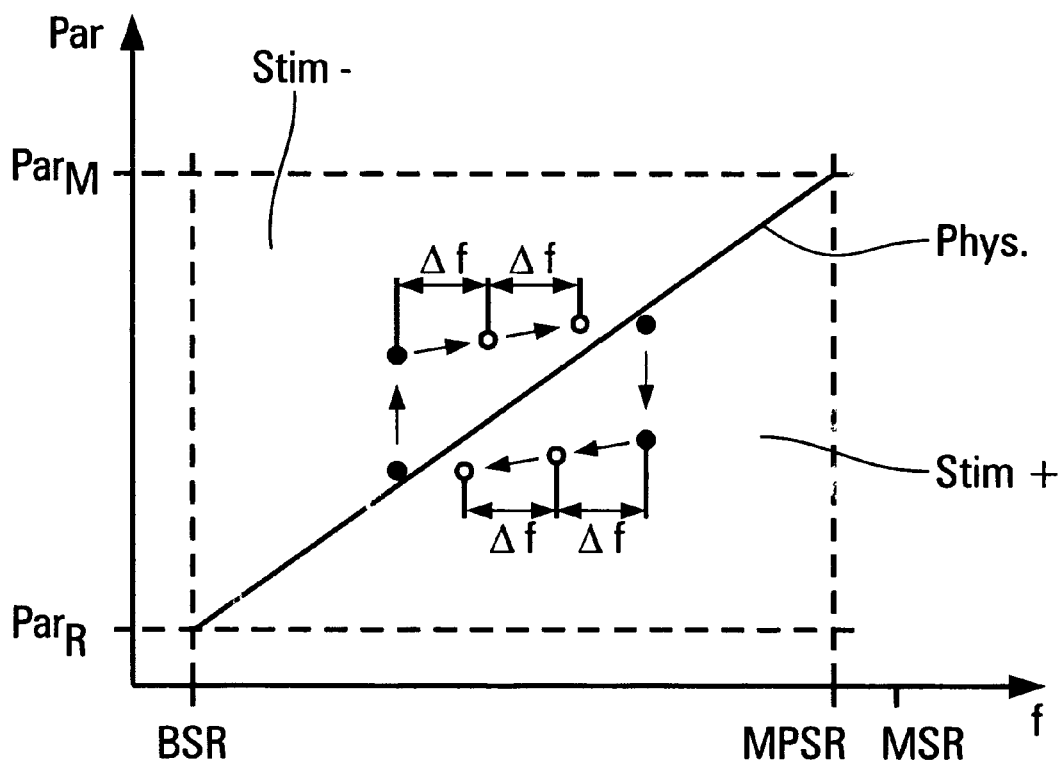
FIG. 6 is a schematic representation of the stimulation rate control, based on one embodiment of the invention.

FIG. 6 is a schematic representation of a preferred method of controlling the stimulation rate f in dependence on an adaptation parameter Par, determined in accordance with the above explanations. The limit values for the adaptation parameter (in the following also called "difference parameter") Par for the resting position ($Par_R$) and the maximum stress ($Par_M$), determined through auto-calibration, together with the predetermined minimum value for the stimulation rate (basic sensor rate=BSR) and the maximum rate determined during the auto-calibration (maximum parameter sensor rate=MPSR) span an area from which the difference parameter for the frequency adaptation is used. A stimulation frequency that is not adapted to the stress state is characterized by a deviation of the difference parameter from the physiological course. An increase in stress, caused by the connected difference parameter increase to the low stimulation range, is clearly recognizable during the frequency adaptation. This is countered with a step-by-step increase in the stimulation frequency by a specific amount Δf, until the difference parameter has again reached the physiological course at the higher stimulation frequency. A decreasing difference parameter results in analogous behavior. The step width Δf can be adapted optionally to the amount by which the difference parameter actually deviates from the physiological course.

Owing to the fact that in addition to the changes in the VER, the stimulation frequency itself also influences the difference parameter to a limited degree, this parameter as a rule does not horizontally approach the physiological course during the step-by-step frequency adaptation, as shown in FIG. 6. If, for example, an increased difference parameter is determined in a first adaptation step, the stimulation frequency is increased, which then results in an additional increase in the difference parameter, and so forth. However, this frequency effect is negligibly small within the limits $Par_R$ and $Par_M$, determined through auto-calibration for the difference parameter.

The auto-calibration is carried out by using the stress signals, obtained with an additional sensor (activity sensor). The following assumptions are made for this:
a) The rest state can be defined through a statistical analysis of the difference parameter. A histogram n (Par) is drawn up for this, which contains the Par values for a predetermined time period (e.g., 1 week).
b) The activity sensor signal (motion signal=MS) is a good reflection of the maximum stress, since this stress primarily has a physical cause. A histogram n(MS) is drawn up from the motion signal values.

Figure 7A:
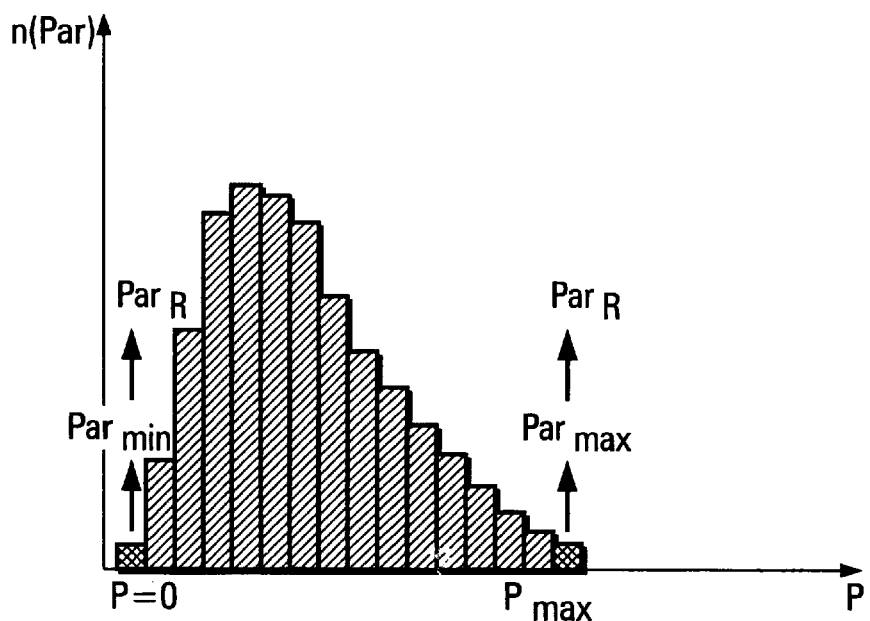
FIGS. 7a and 7b show examples of histograms used for the auto-calibration of the rate-adaptation algorithm.
Figure 7B:
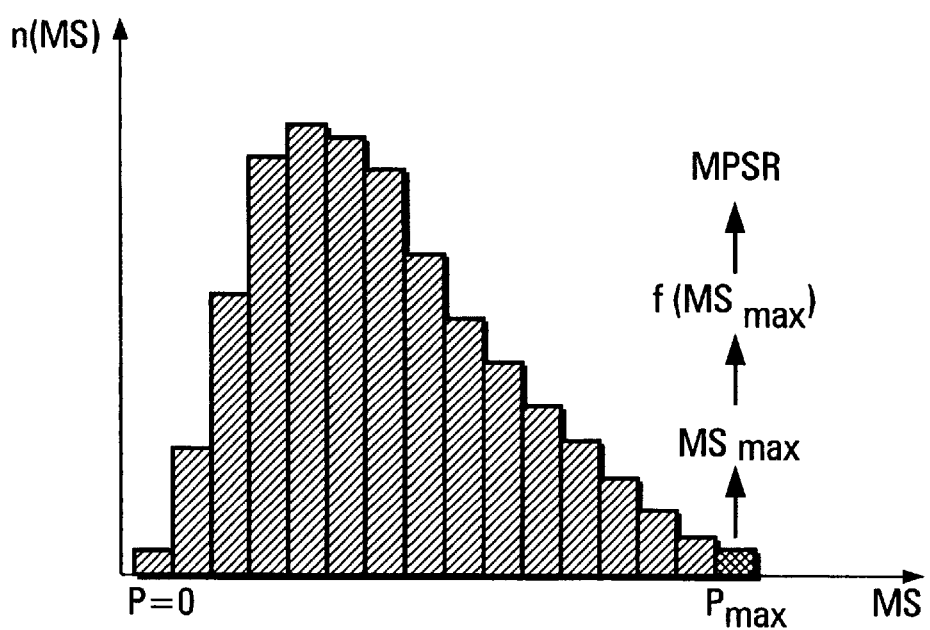

FIGS. 7*a* and 7*b* show examples of the aforementioned histograms.

The frequency limits BSR and MSR, valid for the frequency adaptation, are determined by the physician. The two difference points ($t_1$ or $t_2$ in FIG. 3), as well as the physiological course of the difference parameter are calibrated automatically at predetermined time intervals. That is to say, the difference points are calibrated within sensible limits, in such a way that the load-dependent dynamic of the difference parameter is at a maximum. The determination is made by comparing a VER recorded during the rest state and one recorded for a maximum motion signal, both of which are continuously updated during the pacemaker operation.

Figure 8A:
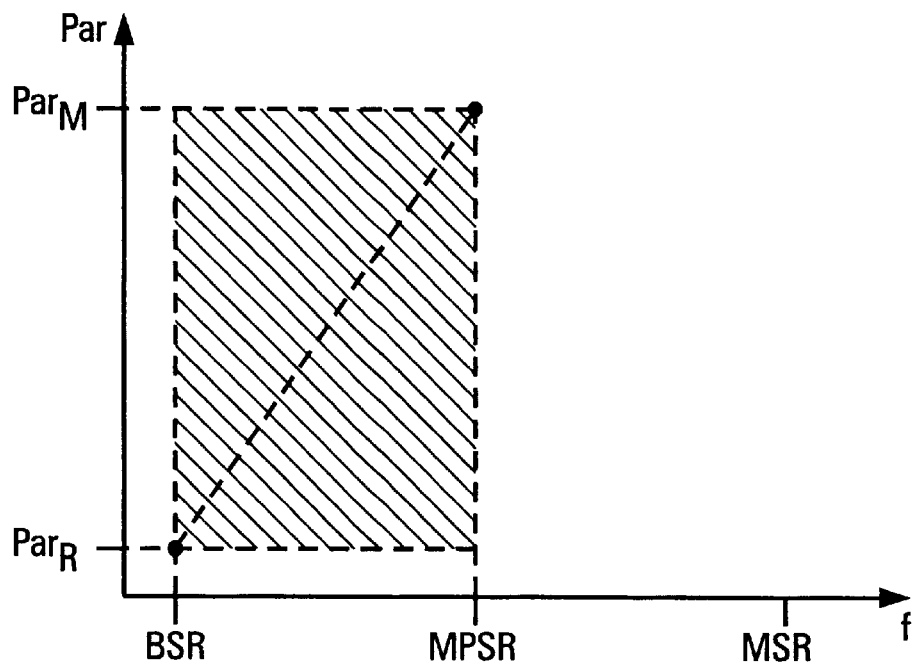
FIGS. 8a and 8b show exemplary embodiments of adaptation parameter frequency dependencies that are relevant within the framework of the auto-calibration.
Figure 8B:
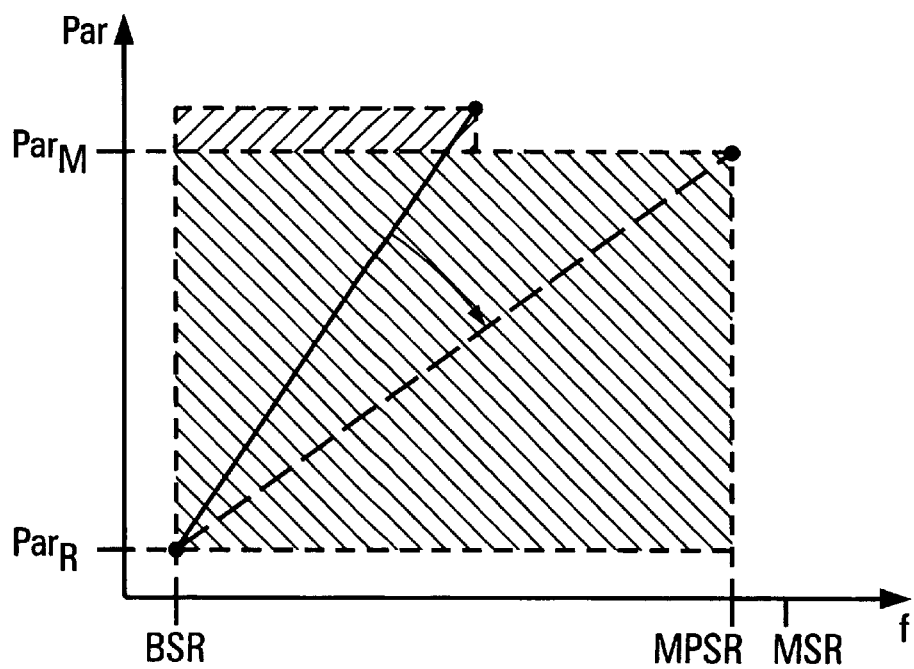

FIGS. 8*a* and 8*b* demonstrate how to obtain the difference parameter values:

The difference parameter for maximum stress (PM) is determined with the aid of the above-mentioned histograms n(Par) and n(MS). The difference parameter value for the rest state ($Par_R$) is initially determined in a first, brief calibration phase (approx. 1 day) with the aid of the histogram n(Par). During continuous operation, this value is then regularly adjusted through auto-calibration. The specified frequency BSR is always assigned to the parameter PR.

Optional starting values are selected for $Par_M$ and MPSR. As a rule, $Par_M$ is selected above the final value that can be expected to result from a long-term operation; MPSR is selected to be nearly in the center of the stimulation frequency range (compare FIG. 8a).

In order to adapt $Par_M$ and MPSR, the highest value $Par_{max}$ occurring in the histogram n(Par) is correlated with the highest value $MS_{max}$ occurring in the histogram n(MS). $P_{max}$ is fixed as the new $Par_M$, while $f(MS_{max})$ is fixed as the new MPSR. Consequently, the area from which the VER frequency adaptation is used is adjusted to the highest values that have occurred for the difference parameter and the motion signal (FIG. 8b). As a result of these steps, the VER frequency adaptation initially has only a relatively low frequency dynamic (low sensitivity to stress) which, however, is increased step-by-step through the auto-calibration, as soon as higher motion signals appear in the histogram n(MS).

The above explanations to the auto-calibration clearly show that for a preferred embodiment of the pacemaker arrangement according to the invention, an additional sensor for a physiological or stress variable is provided besides the means for detecting the evoked intracardiac potentials. The use of this sensor is subject to the following rules:

(1) The continuous recording of the sensor signal in the form of a histogram n(MS) is used for the auto-calibration (see above).
(2) The frequency adaptation is temporarily controlled by the sensor signal if the difference parameter exceeds the value $Par_M$, determined during the calibration. A simple extrapolation of the physiological course to extend past the limits $Par_R$ and $Par_M$ is not permitted.
(3) The frequency adaptation is controlled solely by the sensor signal if no morphology changes or paradox morphology changes are indicated by the VER under stress. The criterion used is a specified minimum dynamic of the difference parameter.
(4) Given specific conditions, the physician selects the sensor such that it only determines the rate adaptation, e.g., to preclude undesirable effects of medications on the VER rate adaptation.

As addressed briefly in the above, the adaptation behavior can be further improved by including a variable representing the signal duration ("signal duration parameter" in the following). In this way, the so-called orthostasis effect can be taken into account in a particularly favorable manner. In a signal morphology change, this orthostasis effect is also present during a change in the body orientation in space (standing, lying down, etc.). Toward the end of the re-polarization phase, the signal duration parameter is defined by the VER, e.g., as the time interval following stimulation and up to the point where the value falls short of a predetermined voltage threshold. It depends on the stress as well as the stimulation frequency. The dependence on the stress is approximated by the dependence on the difference parameter. For the upright body position, the dependencies on the difference parameter and the stimulation frequency are determined separately by auto-calibration and form a two-dimensional function.

The difference parameter increases as soon as the patient changes from the upright to the horizontal body position. However, since the signal duration parameter simultaneously remains unchanged or can even rise slightly, the signal duration parameter deviates directly from the known function for the upright body position. The resting body position is detected as soon as the signal duration parameter increases by more than a specific tolerance value. If the body assumes once more the upright position, the signal duration parameter again drifts into the tolerance range.

In order to correct the orthostasis effect, the physiological course of the difference parameter is raised by a specific offset ("orthostasis shift") when a resting position is detected, as compared to the course for the upright body position. This results in a compensation of the error, occurring in the difference parameter due to the orthostasis effect, while the automatic control mechanism is simultaneously maintained. During the change to the upright body position, the offset is of course canceled again.

Since the evoked heart signals form only during the stimulation and since intrinsic signals cannot be used for the above-outlined determination of the adaptation parameter, a continuous stimulation (with use of the VER, a ventricular stimulation) must be ensured for the continuous frequency adaptation operation, even with adequate natural frequency of the patient. In addition, the occurrence of fusion beats (nearly simultaneous occurrence of stimulation pulse and spontaneous cardiac action) must be avoided because of the non-physiological influencing of the difference parameter connected therewith.

The following options basically exist in the DDD mode:
A1) The AV time for the pacemaker is generally adjusted to be short enough so that the ventricular stimulation is ensured. However, in some instances, this results in a non-physiologically low AV time.
A2) The AV time is adapted to a value just below the physiological value. For that, it is briefly extended at predetermined time intervals by a specified amount. If the pacemaker is blocked during the extended AV time as a result of a ventricular self-action, the time is subsequently reduced to less than the original value to reduce the danger of fusion beats. Otherwise, the originally adjusted value continues to be used.
A3) The AV time is reduced every x beats for y beats by a specific amount, so as to ensure the ventricular stimulation for these y beats and thus also the determination of the adaptation parameter.

The following options exist in the VVI mode:
B1) With ventricular self-action, the stimulation frequency for all x beats is raised for y beats slightly above the natural frequency, so as to be able to determine the difference parameter at regular intervals. The disadvantage in this case is the extended reaction time for the rate adaptation.
B2) The stimulation frequency for ventricular self-action is generally controlled by the signal from the additional sensor instead of the difference parameter.

Even with a suitable use of the options A3) or B1), the case may occur where an up-to-date adaptation parameter is temporarily not available. In order to achieve a reduction in the response time of the rate adaptation algorithm, it is preferable if a stimulation rate tendency, determined in the recent past, continues to be recorded during these time periods. For example, if an increase in the stimulation rate was recorded during the last time period in which the adaptation parameter was available, the stimulation rate is increased further even if there are no up-to-date parameter values.

Figure 9:
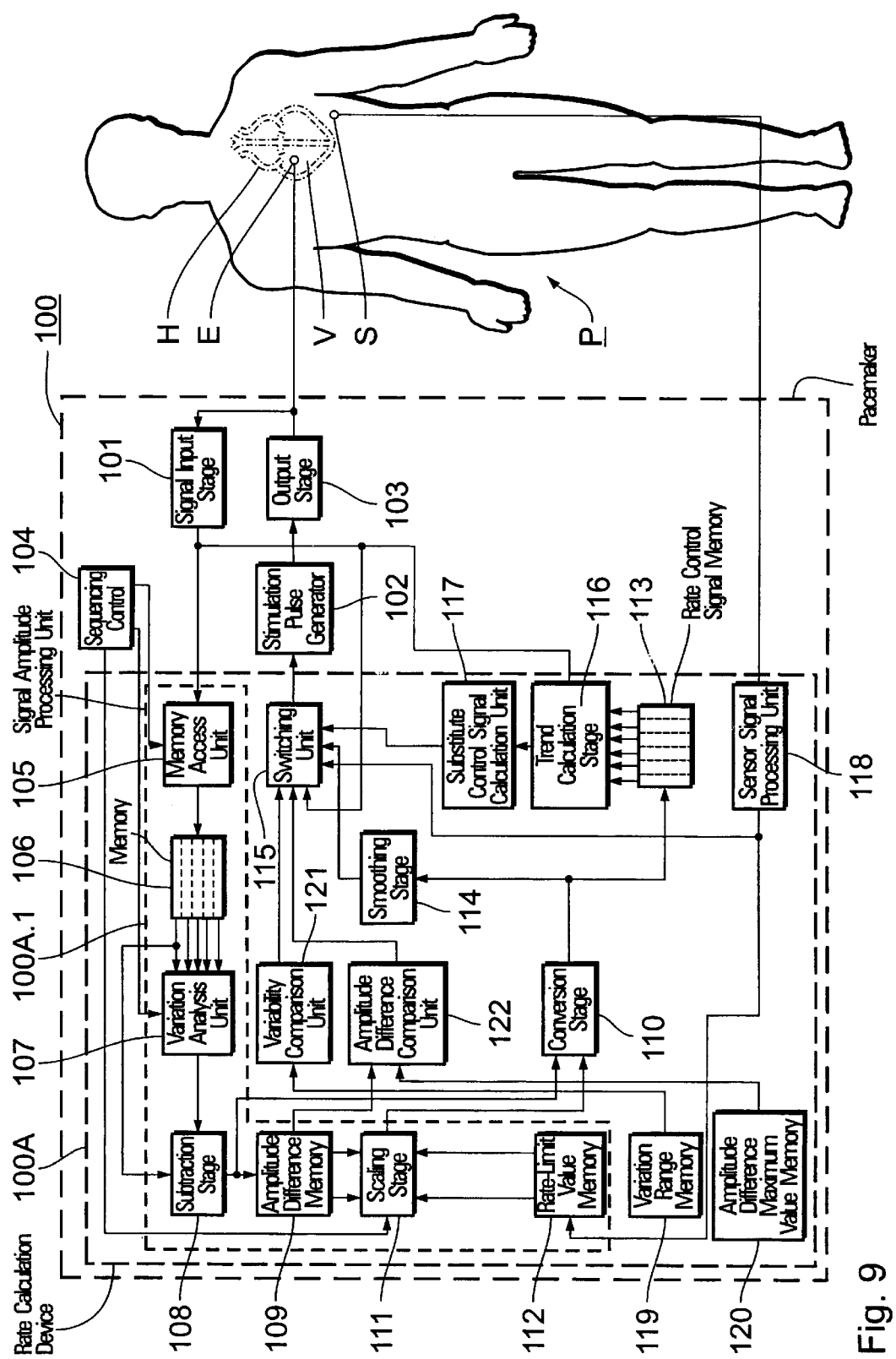
FIG. 9 shows an operational block diagram of essential components of a rate-adaptive pacemaker, based on one embodiment of the invention

FIG. 9 contains an operational block diagram showing essential components of a rate-adaptive pacemaker 100, wherein pacemaker elements that are known per se and are not essential to the embodiment of the invention are left out in the interest of clarity.

The pacemaker 100 is connected on the input side to an intracardiac electrode E in the ventricle V of heart H of a patient P, as well as to an activity sensor S, while on the output side it is simultaneously connected to the electrode E. Ventricular heart signals, acquired with the electrode E, are transmitted to the input of a heart signal input stage 101 (known as such), which is designed for the signal-form correct detection of intracardiac ECG signals. The stimulation pulses generated by a stimulation-pulse generator 102 are transmitted via an output stage 103 and the electrode E to the ventricle V. The pacemaker 100 contains a sequencing control 104 for controlling the complete operational sequence. For reasons of clarity, however, the figure shows only the control signal connections to several components that are important in this connection.

The rate-control signals for controlling the stimulation rate in accordance with the physiological requirement of patient P are generated and made available in a rate-calculation device 100 A, which is connected on the input side with the heart signal input stage 101 as well as the activity sensor S and on the output side with the stimulation pulse generator 102. This rate-calculation device has a signal amplitude processing unit 100A.1 as the most critical functional unit for realizing the invention.

The signal amplitude processing unit 100A.1 comprises a serial cardiac signal memory unit 106, having a plurality of storage areas for, respectively, one complete, evoked ventricular cardiac action (VER). This heart signal memory unit is connected via an A/D converter and memory access unit 105 (which itself is triggered by the sequencing control 104) to the heart signal input stage 101. A variation analysis unit 107 and a subtraction stage 108—also controlled by the sequence control 104—are furthermore connected to the memory unit 106 output. Segments or points in time of the VER signal that show a maximum variability for the difference in the signal amplitudes are determined either once or at specified, longer intervals in the variation analysis unit 107 for a predetermined time interval or a predetermined number of evoked heart signals (corresponding to a program stored in the sequencing control 104). In the subtraction stage 108, the actual amplitude difference value $\Delta U = U_2(t_2) - U_1(t_1)$ for these two cycle times (referred to as adaptation and difference parameters in the above) are formed continuously for the respectively last recorded heart signal U(t). On the output side, the subtraction stage is connected to an amplitude difference memory 109, as well as a conversion stage 110. In the amplitude difference memory 109, the respectively detected highest and lowest amplitude difference values are recorded—updated continuously—and transmitted to a pair of inputs for a scaling stage 111, which is also connected via a second pair of inputs with a rate-limit value memory 112, designed to store the minimum and maximum permissible stimulation rate for the rate control.

In dependence on the stimulation rate, the currently applicable physiological course of the difference parameter is determined in scaling stage 111 from the respectively available minimum and maximum value for the amplitude difference and the minimum and maximum value for the stimulation rates, and is then supplied to the conversion stage 110. In the latter stage, the current rate-control signal is calculated from this as well as from the actual difference parameter value, obtained from the subtraction stage 108, in accordance with the above-explained procedural steps.

On the output side, the conversion stage 110 is connected parallel to a rate-control signal memory 113, as well as a smoothing stage 114. The smoothing stage 114, in which a postprocessing of the rate-control signal takes place (in a manner known per se) to avoid excessive "rate jumps," is connected to an input of a switching unit 115, with which the rate-control signal is finally switched through to the stimulation pulse generator 102 under the conditions as stated in the following.

The rate-control signal memory 113 is connected to the input of a trend calculation stage 116, which is connected to the heart signal input stage 101 via a control signal connection and is activated via this stage if no VER signal is detected. Following its activation, the trend calculation stage 116 loads the stored rate-control signals, coordinated as to time, and performs a trend calculation for this, the result of which is transmitted to a substitute control signal calculation unit 117. By updating the calculated trend, this unit in turn calculates a substitute rate-control signal that is switched through to the stimulation pulse generator by the switching unit 115—also activated via the heart-signal input stage 101—to replace the original rate-control signal that is unavailable if there is no VER signal.

The activity sensor S is connected to a sensor-signal processing unit 118. This unit calculates an additional substitute rate-control signal—based on known algorithms—from the activity signal made available at another input of switching unit 115. The sensor-signal processing unit 118 additionally forms the respectively valid stimulation rate maximum value and transmits this value to the memory 112.

The rate calculation device 100A furthermore comprises a variation range memory 119 and an amplitude difference maximum value memory 120, in which, on the one hand, a minimum permissible amplitude variability value and, on the other hand, the maximum permissible amplitude difference or difference parameter value are stored as marginal conditions that are essential to the application range of the proposed solution. In a variability comparison unit 121 or an amplitude difference comparison unit 122, the stored values are subjected to comparison with the respective actual values, which are supplied by the variation analysis unit 107 or the amplitude difference memory 109 to the comparison units 121, 122. If this comparison shows that one of the required marginal conditions is not met, then the substitute rate-control signal that is generated by the sensor signal processing unit 118 is switched through to the stimulation pulse generator in place of the rate-control signal, calculated on the basis of the signal morphology, in that a respective control signal is issued by the comparison units 121, 122 to the switching unit 115.

Figure 10:
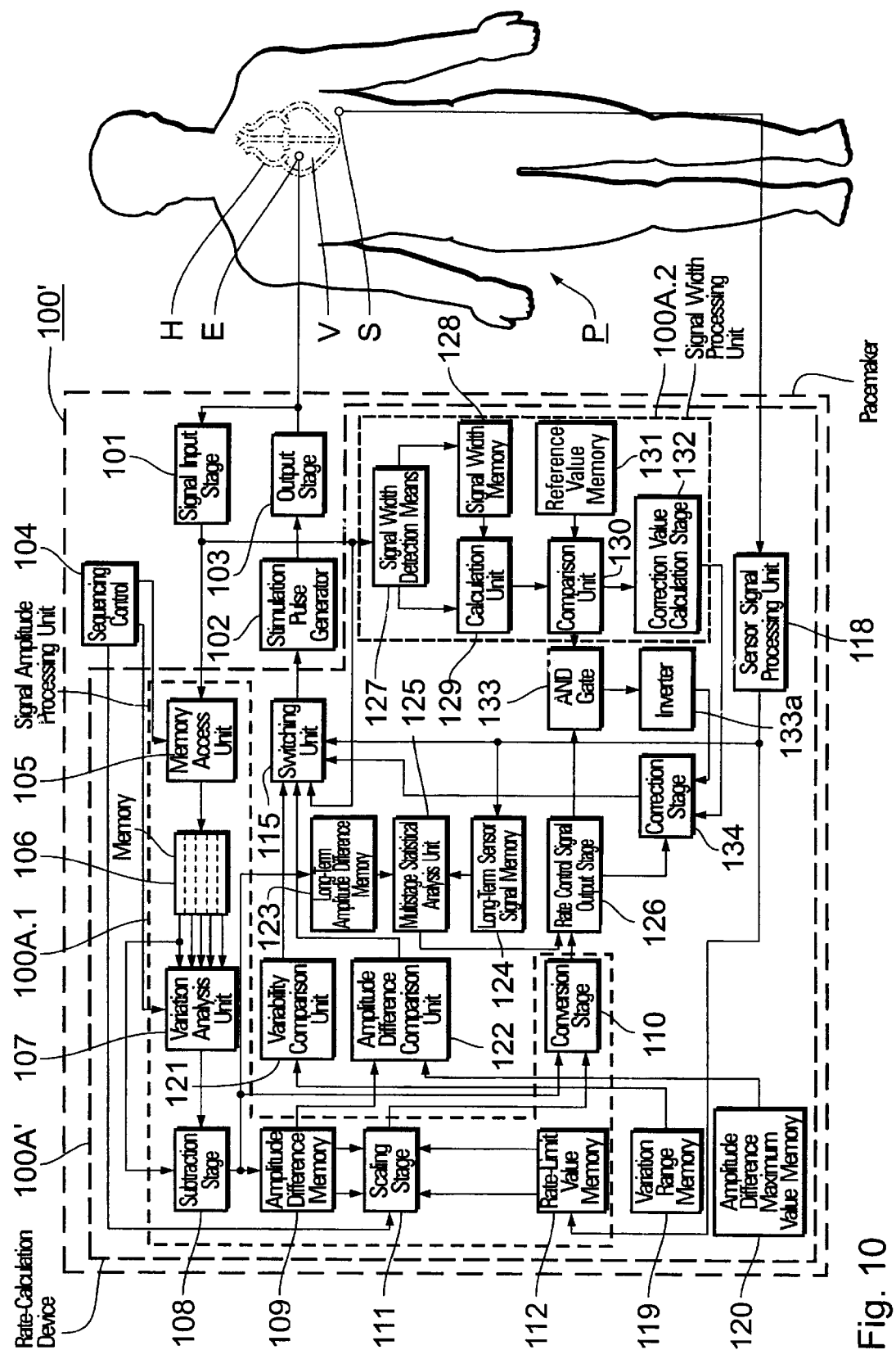
FIG. 10 shows an operational block diagram of a pacemaker, based on another embodiment of the invention.

FIG. 10 shows a diagram of a pacemaker 100' that is modified as compared to the embodiment shown in FIG. 9. The functional components coinciding with those in FIG. 9 were given the same reference numbers and are not explained again.

A first group of additional components comprises a long-term amplitude difference memory 123, which is connected to the output of the subtraction stage 108, a long-term sensor-signal memory 124 that is connected to the output of sensor-signal processing unit 118, as well as a multistage statistical analysis unit 125, which is connected to both long-term memories and is used to form an amplitude difference histogram and a sensor-signal histogram and to establish a correlation between both histograms, wherein the rate-control signal is generated in dependence on the established correlation. A rate-control signal output stage 126 finally supplies the rate-control signal required for controlling the stimulation pulse generator 102, based on the analysis of the signal morphology. This rate-control signal is subsequently transmitted to the pulse generator via the switching unit 115, the basic function of which is explained above with reference to FIG. 9.

Signal-width detection means 127 for detecting the actual heart signal width are connected in series after the heart signal input stage 101. The rate-calculation device 100A additionally has a signal width processing unit 100A.2 for generating the rate-control signal by taking into account the heart signal width.

The signal width processing unit 100A.2 comprises a signal width memory 128, connected to the signal width detection means 127, a calculation unit 129 that is connected to the signal width detection means 127 and the signal width memory 128, and a comparison unit 130 that is connected to the calculation unit 129 and the reference value memory 131 for comparing a variable that depends on the actual signal width to a reference value. An AND gate 133 is connected to the outputs of the signal amplitude processing unit 100A.1 and the signal width processing unit 100A.2, which permits the direct output of the rate-control signal generated by the signal amplitude processing unit 100A.1, but only if the comparison result has a predetermined quality, specifically, if the signal width does not fall below a predetermined value.

The signal width processing unit 100A.2 furthermore has a correction value calculation stage 132. The output of this stage, together with the output of the signal amplitude processing unit 100A.1, is conducted to a correction stage 134 which is connected via an inverter 133a to the output of the AND gate 133. If the comparison result does not have the aforementioned predetermined quality, a correction of the rate-control signals generated by the signal amplitude processing unit 100A.1 is effected.

The invention in its embodiment is not limited to the aforementioned, preferred exemplary embodiments. Rather, a plurality of variants are conceivable, which make use of the presented solution, even if the embodiments are basically very different.

What is claimed is:

1. A rate-adaptive pacemaker comprising:
   a stimulation pulse generator for stimulating at least the ventricle of a heart;
   output means connected to said stimulation pulse generator for supplying a stimulation pulse to said heart;
   a heart-signal input stage for detecting the shape of evoked heart signals;
   a rate calculation device, receiving as input an output from said heart-signal input stage and providing an output to said stimulation pulse generator, said output including a rate-control signal, said rate calculation device calculating a stimulation rate based on physiological stress of an individual in whom the pacemaker is implanted and including a signal-amplitude processing unit for calculating the rate-control signal in response to heart signal amplitude values at predetermined times during a specified heart cycle, said heart signal amplitude values derived in connection with said shape of evoked heart signals.

2. A rate-adaptive pacemaker according to claim 1, wherein said heart-signal input stage detects the morphology of the ventricular evoked response (VER).

3. A rate-adaptive pacemaker according to claim 1, wherein said specified heart cycle is the immediately preceding heart cycle.

4. A rate-adaptive pacemaker according to claim 1, said signal-amplitude processing unit comprising a subtraction stage for determining a heart-signal amplitude difference at two predetermined points in time during the heart cycle.

5. A rate-adaptive pacemaker according to claim 4, said signal-amplitude processing unit comprising:
   a heart signal memory for storing a plurality of heart signal curves; and
   a variation analysis unit connected to said heart signal memory and determining for a predetermined time period or a predetermined number of evoked heart signals two cycle times of the heart signal for which the difference in heart signal amplitudes shows maximum variability.

6. A rate-adaptive pacemaker according to claim 5, said rate calculation device further comprising:
   stimulation-rate storage means storing lower and upper limit values for stimulation rate;
   amplitude difference storage means storing minimum and maximum heart signal amplitude difference values; and
   a scaling stage receiving inputs from said stimulation-rate storage means and from said amplitude difference storage means, the scaling stage determining a physiologically standardized dependence of the heart signal amplitude difference on the adapted stimulation rate for the predetermined time period or the predetermined number of heart cycles, in that it links the stored minimum and maximum heart signal amplitude difference values with the stored lower and upper limit values for stimulation rate and derives the rate-control signal based on a deviation between the actually determined heart-signal amplitude difference and the physiologically scaled dependence.

7. A rate-adaptive pacemaker according to claim 6, said rate calculation device further comprising a smoothing stage, said smoothing stage emitting a rate-control signal signal that effects a stage-by-stage adaptation of the stimulation rate in response to said deviation exceeding a predetermined amount.

8. A rate-adaptive pacemaker according to claim 1, wherein said heart signal input stage is arranged to detect at least the R+ wave of the VER and said rate calculation device is arranged to generate said rate-control signal in response to a heart signal amplitude difference detected during a current heart signal segment.

9. A rate-adaptive pacemaker according to claim 1, wherein there are predetermined cycle times that are kept invariant relative to changes in the stimulation rate.

10. A rate-adaptive pacemaker according to claim 1, further comprising:
    an additional sensor, said additional sensor connected to an input of said rate calculation device, said additional sensor arranged to detect a parameter that depends on the physiological stress; and
    said rate calculation device further comprising means for taking into account a signal from said additional sensor when generating a rate-control signal.

11. A rate-adaptive pacemaker according to claim 10, said rate calculation device further comprising:
    a maximum rate determination stage, which determines an upper limit value for stimulation rate for said predetermined time period or said predetermined number of heart cycles based on a maximum value that has occurred for said physiological stress-dependent parameter.

12. A rate-adaptive pacemaker according to claim 10, said rate calculation device further comprising:
    a maximum value memory that stores a maximum permissible amplitude difference value for stimulation rate adaptation based on heart signal shape;
    an amplitude difference comparison unit connected to said maximum value memory, said amplitude difference comparison unit comparing the actually determined amplitude difference value to the stored maximum amplitude difference value; and a switching unit controllable by the output of said amplitude difference comparison unit to transmit a substitute rate-control signal to the stimulation pulse generator if the maximum amplitude difference value is exceeded, said substitute rate-control signal being calculated based on said signal from said additional sensor.

13. A rate-adaptive pacemaker according to claim 10, said rate calculation device further comprising:

a minimum value memory that stores a minimum permissible amplitude difference value for stimulation rate adaptation based on heart signal shape;

an amplitude difference comparison unit connected to said minimum value memory, said amplitude difference comparison unit comparing the actually determined amplitude difference value to the stored minimum amplitude difference value; and a switching unit controllable by the output of said amplitude difference comparison unit to transmit a substitute rate-control signal to the stimulation pulse generator if said minimum amplitude difference value is not exceeded, said substitute rate-control signal being calculated based on said signal from said additional sensor.

14. A rate-adaptive pacemaker according to claim 10, said rate calculation device further comprising:

a long-term amplitude difference memory;

a long-term sensor signal memory; and a multistage statistical analysis unit, connected to both long-term memories and used to form an amplitude difference histogram and a sensor signal histogram and to establish a correlation between said histograms, wherein the rate-control signal is generated based on the established correlation.

15. A rate-adaptive pacemaker according to claim 1, said rate calculation device further comprising:

at least one of an amplitude difference memory and a rate-control signal memory;

a trend calculation stage connected to said at least one of an amplitude difference memory and a rate-control signal memory and generating, respectively, at least one of an amplitude difference trend and a rate-control signal trend;

a substitute control signal calculation unit connected to the output of said trend calculation stage; and a switching unit receiving as an input an output of at least one of said stimulation pulse generator output and said heart-signal input stage, wherein if the stimulation pulse generator is blocked or an evoked heart signal is not detected, the rate-control signal is an output of said substitute control signal calculation unit generated by updating said at least one of an amplitude difference trend and a rate-control signal trend.

16. A rate-adaptive pacemaker according to claim 1, further comprising:

signal-width detection means connected in series following the heart signal input stage and serving to detect an actual heart signal width, beginning with the emitting of a stimulation pulse or the exceeding of a predetermined signal start amplitude, and ending by falling below a predetermined signal end amplitude; and wherein said rate calculation device further comprises:
a signal-width processing unit that generates a rate control signal based on said actual heart signal width.

17. A rate-adaptive pacemaker according to claim 16, said signal-width processing unit comprising:

a signal-width memory connected to said signal-width detection means;

a calculation unit connected to said signal-width detection means and to said signal-width memory;

a reference value memory; and a comparison unit connected to said calculation unit and said reference value memory, said comparison unit comparing an output of said calculation unit that depends on actual signal width to a reference value stored in said reference value memory and generating a comparison result; and said rate calculation device further comprising:

an AND gate receiving as inputs signal from said signal-amplitude processing unit and said signal-width processing unit, said AND gate permitting the direct output of the rate-control signal generated by the signal-amplitude processing unit, provided that the comparison result of said comparison unit has a predetermined quality.

18. A rate-adaptive pacemaker according to claim 17, said signal-width processing unit further comprising:

a correction value calculation stage; and a correction stage receiving as input an output of said correction value calculation stage; and an inverter connecting an output of said AND gate to an input of the correction stage, wherein if said comparison result does not have said predetermined quality, a correction of a rate-control signal generated by the signal-amplitude processing unit is effected.

* * * * *